United States Patent [19]
Northrup, III et al.

[11] Patent Number: 5,972,024
[45] Date of Patent: Oct. 26, 1999

[54] SUTURE-STAPLE APPARATUS AND METHOD

[75] Inventors: William F. Northrup, III; Joanne B. Northrup; Jeffrey J. Northrup, all of Edina, Minn.

[73] Assignee: Metacardia, Inc., Edina, Minn.

[21] Appl. No.: 08/998,109

[22] Filed: Dec. 24, 1997

Related U.S. Application Data

[60] Provisional application No. 60/034,354, Dec. 24, 1996.

[51] Int. Cl.$^6$ ........................................ A61B 17/04
[52] U.S. Cl. ..................... 606/232; 606/151; 606/219; 606/220; 606/228
[58] Field of Search ..................... 606/232, 144, 606/222, 228, 151, 219, 220, 157

[56] References Cited

U.S. PATENT DOCUMENTS

| | | | |
|---|---|---|---|
| 4,732,151 | 3/1988 | Jones | 606/222 |
| 4,901,721 | 2/1990 | Hakki | 606/103 |
| 5,074,874 | 12/1991 | Yoon et al. | 606/224 |
| 5,123,913 | 6/1992 | Wilk et al. | 606/232 |
| 5,269,809 | 12/1993 | Hayhurst et al. | 606/232 |
| 5,500,000 | 3/1996 | Feagin et al. | 606/232 |
| 5,665,109 | 9/1997 | Yoon | 606/232 |
| 5,810,853 | 9/1998 | Yoon | 606/232 |

*Primary Examiner*—Gary Jackson
*Attorney, Agent, or Firm*—Patterson & Keough, P.A.

[57] ABSTRACT

A staple for effecting e.g. an anastomosis between two vascular structures is combined with a delivery system for the staple, the delivery system comprising a suture having a needle connected thereto at one end. The needle is constructed for passage through an edge of each vascular structure, and further is constructed to pull the suture through the vascular structures. The staple according to one embodiment is connected to an end of the suture opposite the needle. After being drawn into place by the suture, the staple is hooked into a desired position with respect to the vascular structures such that the staple is engaged on both sides of the anastomosis. The staple then is crimped to form substantially a loop around the edge of the anastomosis to hold the vascular structures together, both internally and externally. The suture is constructed for ready separation from the staple once the staple is crimped. Once separated, e.g. by cutting, the delivery system is removed from the staple. The staple remains in place to hold the vascular structures together and provide a secure and substantially sealed anastomosis.

29 Claims, 4 Drawing Sheets

SUTURE-STAPLE APPARATUS AND METHOD

CROSS-REFERENCE TO RELATED APPLICATION

The subject matter of this application is related to the subject matter of commonly assigned U.S. Application Ser. No. 60/034,354, filed Dec. 24, 1996, priority to which is claimed under 35 U.S.C. § 119(e) and which is incorporated by reference herein in its entirety.

BACKGROUND OF THE INVENTION

1. Field of the Invention

The invention relates to devices and methods for joining two anatomical structures together, and more particularly, according to one embodiment, to devices and methods for effecting an anastomosis of two anatomical structures without multiple knots. Embodiments of the invention are applicable in minimally invasive surgical situations, and in conventional surgical situations as well.

2. Description of Related Art

The use of sutures and staples individually in cardiothoracic surgical situations is known, of course, in the art. Sutures typically terminate in a curved needle, which is used to pierce the tissue or other anatomical structure and draw the suture therethrough. After placing a desired number of sutures in appropriate locations, as needed for a particular surgical procedure, the surgeon draws each suture tight and ties one or more surgical knots. The surgeon can choose from a wide variety of commercially available sutures, knots and needles.

Similarly, a number of different staples are known for closing surgical incisions and performing other closure functions. The ends of a staple suitable for a particular surgical application are bent or crimped to hold two regions of tissue together or otherwise to fix different tissues in a desired positional relationship.

Known staples generally are placed into proper position from the outside of the incision or other opening to be closed. In other words, the surgeon approaches the incision with the staple externally and crimps the staple, e.g. with a surgical stapling device, to form a seal of external origin. This presents a significant disadvantage, in that the external application of the staple is "blind" and therefore substantially prevents precise approximation (i.e. precise bringing together) of the inner layers of the two tissue structures. This "outside-in" staple application also creates risk of infolding (inversion) of tissue and associated compromise of the anastomosis by obstruction.

For the first time, embodiments of the invention overcome the above and other disadvantages by placing the staple "inside-out," substantially guaranteeing precise approximation of the inner layer of e.g. two structures anastomosed to each other by eversion and substantially preventing inversion of obstructing tissue. Embodiments of the invention also are simpler, more cost-effective and less time-consuming to use, and also can reduce the amount of trauma to which tissues are subjected.

SUMMARY OF THE INVENTION

To achieve these and other advantages, a staple for effecting e.g. an anastomosis between two vascular structures is combined with a delivery system for the staple, the delivery system comprising a suture having a needle connected thereto at one end. The needle is constructed for passage through an edge of each vascular structure, and further is constructed to pull the suture through the vascular structures. The staple according to one embodiment is connected to an end of the suture opposite the needle.

Preferably after being drawn into place by the suture, the staple is hooked into a desired position with respect to the vascular structures such that the staple is engaged on both sides of the resulting anastomosis, according to one embodiment. The staple then is crimped to form substantially a loop around the edge of the anastomosis to hold the vascular structures together. Crimping the staple preferably causes two limbs of the staple to move into proximity with each other, and, according to one embodiment, the two limbs of the staple form a substantially acute angle even before the staple is crimped.

The suture is constructed for ready separation from the staple once the staple is crimped. Once separated, e.g. by cutting, the delivery system is removed from the staple. The staple remains in place to hold the vascular structures together and provide a secure and substantially sealed anastomosis, according to one embodiment.

According to another aspect of the invention, an apparatus for joining at least two anatomical structures includes a suture having a first end and a second end, the suture being constructed for passage through the anatomical structures. A needle is provided for penetrating and passing through the anatomical structures, the needle being disposed at the first end of the suture and having a sharp tip.

A holding device for holding the anatomical structures together, e.g. a staple in one embodiment, is disposed at the second end of the suture for placement into proximity with the anatomical structures. The holding device is constructed for movement from an initial configuration to a holding configuration, wherein movement of the holding device from the initial configuration to the holding configuration causes the anatomical structures to be joined together. The holding device preferably includes staple structure comprising a bendable material, the movement between configurations comprising bending of the staple. The holding device preferably holds the anatomical structures together from inside the anatomical structures.

According to another embodiment, the holding device includes a cross-piece, the cross-piece being constructed for anchoring to at least one of the anatomical structures when the holding device is in the holding configuration. More specifically, the holding device is constructed substantially to prevent at least a distal portion of the holding device from tearing through the anatomical structures.

Finally, according to method embodiments of the invention, a method for joining at least two anatomical structures includes penetrating the anatomical structures with a needle having a sharp tip and passing the needle through the anatomical structures. A suture having a first end and a second end is passed through the anatomical structures, the needle being disposed at the first end of the suture. The anatomical structures are held together with a holding device disposed at the second end of the suture, by placing the holding device into proximity with the anatomical structures and moving the holding device from an initial configuration to a holding configuration. Movement of the holding device from the initial configuration to the holding configuration causes the anatomical structures to be joined together. According to one embodiment, the method also includes parachuting the sutures connected to respective holding devices by pulling the anatomical structures apart, to assess e.g. proper positioning and spacing of the sutures and/or holding devices.

BRIEF DESCRIPTION OF THE DRAWINGS

Embodiments of the invention will be described with respect to the figures, in which like reference numerals denote like elements and in which.

DETAILED DESCRIPTION OF PREFERRED EMBODIMENTS

Embodiments of the invention particularly apply to effecting an anastomosis of two vascular structures, for example blood vessels in the cardiothoracic region during a MID-CAB (minimally invasive direct coronary artery bypass) procedure. Embodiments of the invention apply to a wide variety of surgical situations, however, not just those involving anastomoses and vascular structures. Therefore, although embodiments of the invention will be described with respect to anastomoses and vascular structures, the invention is by no means limited to such embodiments.

Figure 1:
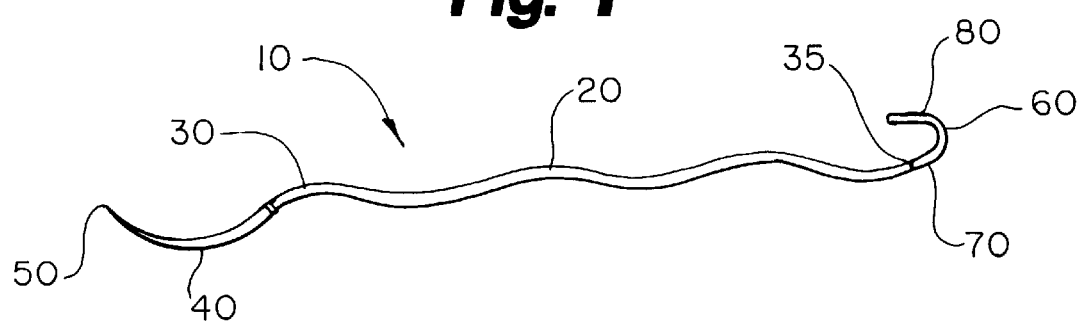
FIG. 1 is a side view of an apparatus for joining anatomical structures together, according to an embodiment of the invention.

FIG. 1 is a side view of an apparatus for joining at least two anatomical structures, according to an embodiment of the invention. Apparatus 10 includes suture 20 having first end 30 and second end 35, suture 20 being constructed for passage through anatomical structures in a manner to be described. Suture 20 can be formed of a wide variety of materials, e.g. monofilament materials having minimal memory, e.g. polypropylene or polyamide. Any appropriate diameter size can be used, e.g. 2-0 through 8-0. Other suture types and sizes are also possible, of course, and are equally contemplated by the invention.

Needle 40 preferably is curved and is disposed at first end 30 of suture 20. Sharp tip 50 of needle 40 enables easy penetration of various anatomical structures and enables needle 40 and suture 20 readily to pass therethrough. Needle 40 can be attached to suture 20 in various ways, for example by swedging, preferably substantially matching the outer diameter (o.d.) of needle 40 and suture 20 as closely as possible.

Apparatus 10 also includes holding device 60 disposed at second end 35 of suture 20. Holding device 60 includes first and second limbs 70, 80, according to the illustrated embodiment, and preferably is of greater stiffness than suture 20. First limb 70 can be connected to suture 20 in a number of ways, for example by swedging, preferably substantially matching the o.d. of suture 20 and holding device 60 as closely as possible. Holding device 60 includes staple structure comprising a bendable material that preferably is soft and malleable enough to crimp and hold its crimped position on the outside of an anastomosis. Such materials can include e.g. titanium or stainless steel. Holding device 60 can be called a staple, according to the illustrated embodiment, and suture 20 and needle 40 a delivery system for staple 60.

FIG. 1 illustrates one of the many possible initial configurations of holding device 60, i.e. the configuration holding device 60 is in upon initial passage through the anatomical structures and/or at a point in time beforehand. As will be described, holding device 60 is movable from the initial configuration to a holding configuration, in which holding device 60 holds the anatomical structures together. According to the illustrated embodiments, holding device 60 assumes the holding configuration when it is bent or crimped, as shown in e.g. FIG. 6 (further described below).

Holding device 60 preferably is V-shaped or U-shaped, as illustrated, but can assume a wide variety of shapes to suit particular surgical situations and/or surgeon preference. For example, one of limbs 70, 80 can be straight and the other curved, or limbs 70, 80 can be collinear. Holding device 60 preferably is as smooth and round in cross-section as needle 40. Further, the diameters of needle 40, suture 20, and holding device 60 preferably are substantially identical, especially needle 40 and holding device 60, to avoid creating holes in the anatomical structures that are larger than the diameter of staple 60. Such holes likely would cause bleeding and/or leakage.

Figure 2:
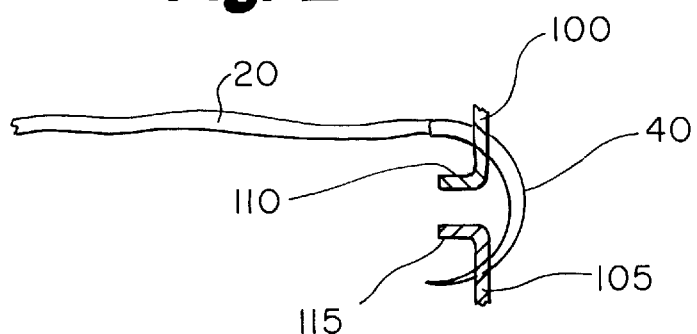
FIG. 2 is a cross-sectional view showing a needle portion of the FIG. 1 apparatus passing through edges of anatomical structures, according to an embodiment of the invention.
Figure 3:
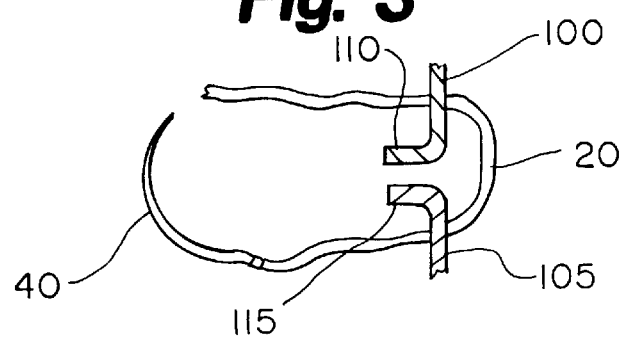
FIG. 3 is a cross-sectional view showing the FIG. 1 apparatus pulled through an anastomosis, according to an embodiment of the invention.
Figure 4:
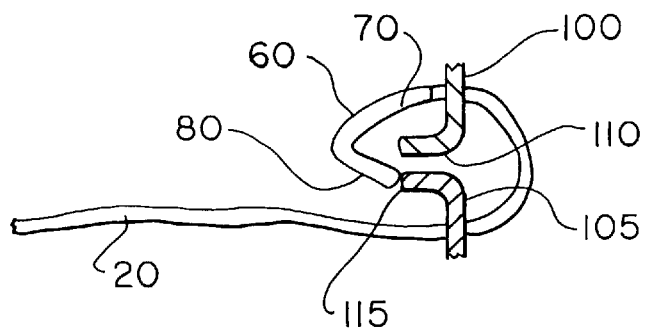
FIG. 4 is a cross-sectional view showing a staple of the FIG. 1 apparatus being placed into proximity with the anatomical structures, according to an embodiment of the invention.
Figure 5:
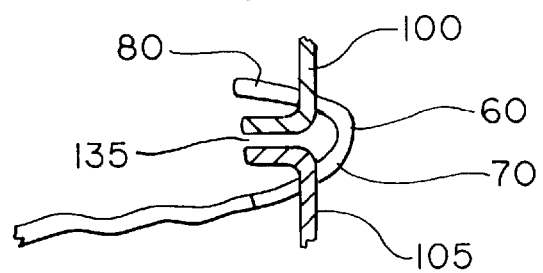
FIG. 5 is a cross-sectional view showing a staple of the FIG. 1 apparatus being engaged on both sides of the anastomosis, according to an embodiment of the invention.

A preferred method of using apparatus 10 is illustrated in e.g. FIGS. 2–6. First, as shown in FIG. 2, needle 40 passes through anatomical structures 100, 105, which are e.g. vascular structures. Specifically, according to the illustrated embodiment, needle 40 passes through edges 110, 115 of vascular structures 100, 105. Then, as shown in FIG. 3, needle 40 pulls suture 20 into and through both structures 100, 105. Staple 60 then is pulled into desired proximity with structures 100, 105, as shown in FIGS. 4–5, such that it is engaged on both sides of the illustrated anastomosis and associated lumen 135. According to one embodiment, traction is placed on suture 20 to hook staple 60 into position.

Figure 6:
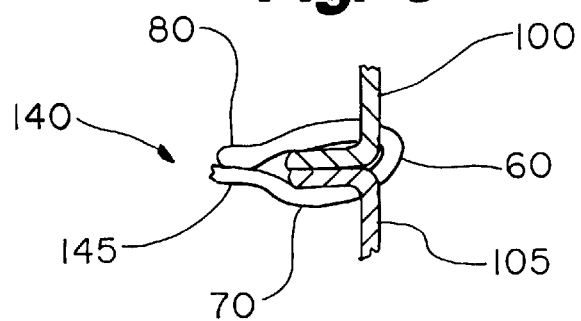
FIG. 6 is a cross-sectional view showing a staple after it has been crimped to join the anatomical structures, according to an embodiment of the invention.

As shown in FIG. 6 and as referenced earlier, staple 60 then is moved from its initial configuration to a holding or crimped configuration 140, in which anatomical structures 100, 105 are joined together to effect an anastomosis between them. Staple 60 creates substantially a 360-degree loop at the edge of the anastomosis, with crimped portion 145 outside lumen 135. A wide variety of tools and/or mechanisms can be used to crimp staple 60 into its holding configuration, e.g. in the manner of closure of a vascular clip. The same tool, or an alternative tool, can then be used to separate staple 60 from suture 20, e.g. by cutting.

Thus, staple 60 holds vascular structures 100, 105 together from inside the vascular structures, as well as from outside, unlike the many prior art staples that secure opposed structures only externally. This achieves a number of advantages, as described above. Not only does a better approximation result, but e.g. crimping a staple is simpler than tying one or more knots and also likely is less traumatic on tissue. Staple closure with a single crimp provides less tension on an anastomosis, for example, than a knot requiring several throws. Embodiments of the invention are especially advantageous in minimally invasive surgical situations, as knot-tying with e.g. a knot pusher in a minimally invasive setting through a small port is particularly tedious and can require up to four or five throws to prevent slippage. Crimping a staple through the port, as with embodiments of the invention, is far simpler and eliminates much of the difficulty.

According to one embodiment, the surgeon achieves a precise approximation of the vascular or other structures with preferably a limited number of staples or other holding devices, and then completes the e.g. anastomosis with biologic glue or laser techniques. The holding devices, e.g. two or more in number, can be used to orient or line up the structures initially and thus used as a "pilot" for guiding the completion of the anastomosis.

Figure 7:
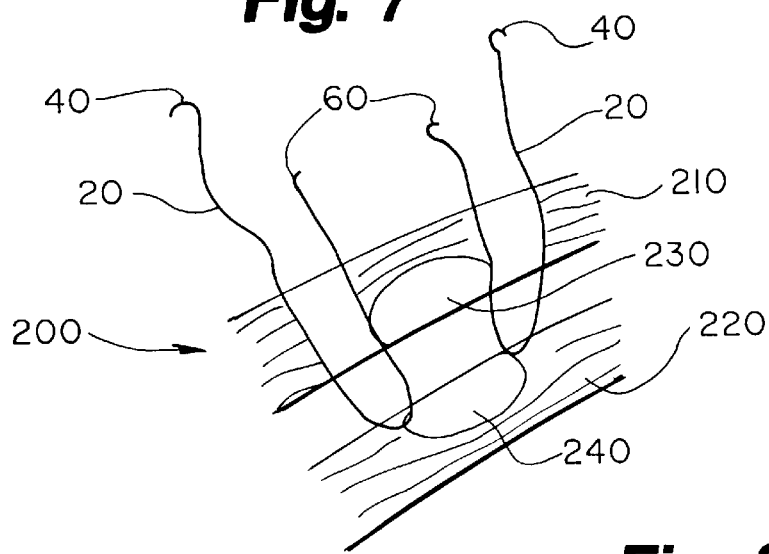
FIG. 7 is a perspective view of a side-to-side anastomosis, according to an embodiment of the invention.
Figure 8:
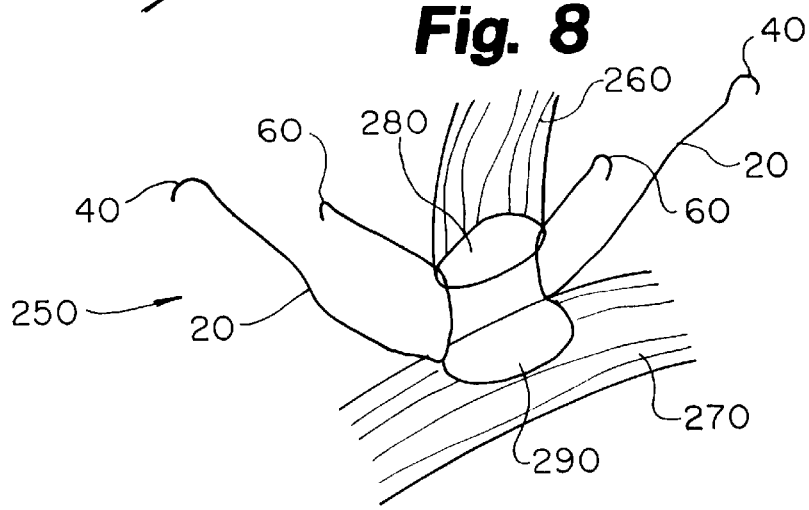
FIG. 8 is a perspective view of an end-to-side anastomosis, according to an embodiment of the invention.
Figure 9:
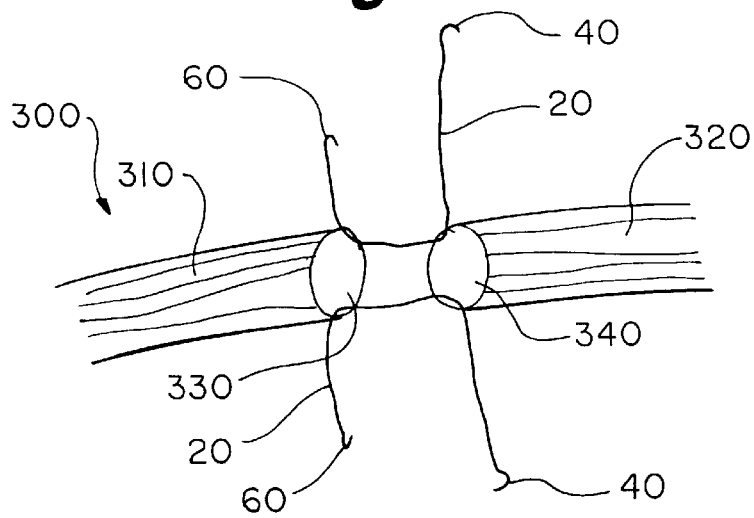
FIG. 9 is a perspective view of an end-to-end anastomosis, according to an embodiment of the invention.

FIGS. 7–9 show plural uses of apparatus 10 to effect side-to-side, end-to-side, and end-to-end anastomoses 200, 250, 300, respectively. Specifically, as shown in FIG. 7, side-to-side anastomosis 200 is effected between vascular structures 210, 220 to join lumens 230, 240. The end-to-side anastomosis 250 of FIG. 8 is between structures 260, 270 and their corresponding lumens 280, 290. Finally, the end-to-end anastomosis 300 of FIG. 9 shows sutures 20 used to join structures 310, 320 with respective lumens 330, 340.

Once sutures 20 are appropriately placed, sutures 20 can be "parachuted" by pulling the respective vascular structures apart, in order to check for proper positioning and spacing of sutures 20 and/or holding devices 60. This also enables the surgeon to check for crosses, tangles, etc. in sutures 20 themselves.

Figure 10:
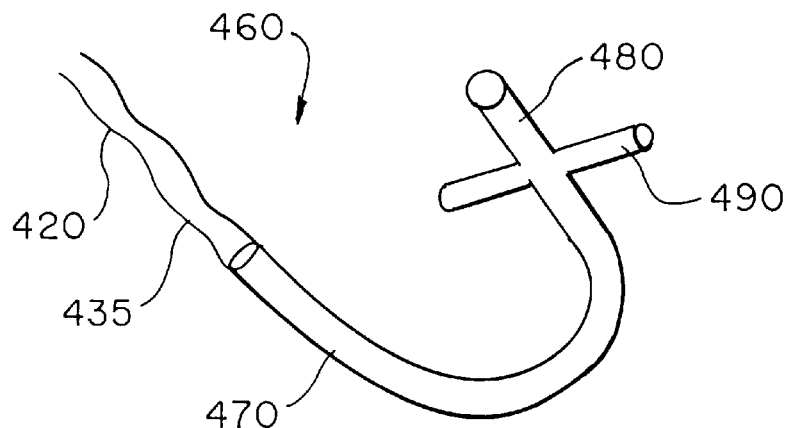
FIG. 10 is a perspective view of a staple according to an embodiment of the invention.
Figure 11:
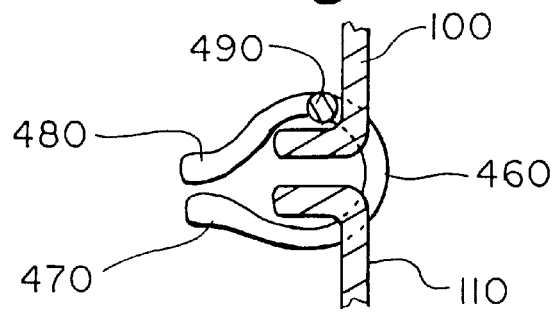
FIG. 11 is a cross-section showing an anastomosis secured by a FIG. 10 staple, according to an embodiment of the invention.
Figure 12:
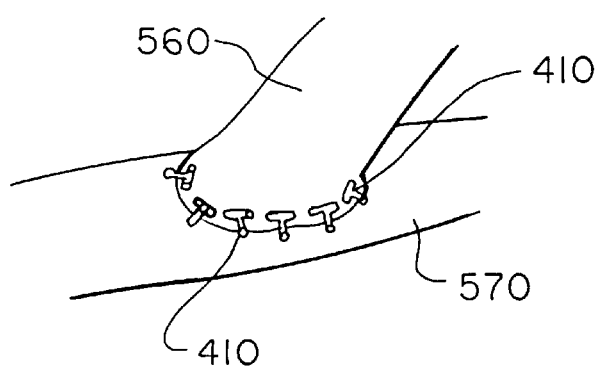
FIG. 12 is a perspective view of an end-to-side anastomosis using a plurality of the FIG. 10 staples.

Finally, FIGS. 10–12 illustrate an alternative holding device embodiment, disposed on suture 420 at end 435 e.g. by swedging. Holding device or staple 460 includes two limbs 470, 480, the latter of which includes cross-piece 490 that preferably is disposed substantially transversely to limb 480. As shown in FIGS. 11–12, cross-piece 490 serves better to anchor staple 460 against vascular structure 100 first penetrated by the needle. Cross-piece 490 preferably lies in the plane of the anastomosis when engaged, as shown. Cross-piece 490 thus provides a buttress, substantially preventing the needle from tearing through the vascular structure(s), e.g. structures 560, 570 in the end-to-side anastomosis illustrated in FIG. 12.

While the invention has been described with respect to specific embodiments, the invention is by no means limited to the specific embodiments illustrated and described herein. For example, embodiments of the invention apply not only to anastomoses of vascular structures in e.g. minimally invasive thoracic surgical situations, but also to conventional surgical techniques and to anatomical structures other than vascular structures. One or more of the devices 10 can be linked together, e.g. by readily severable or non-severable connectors, for simultaneous application of multiple holding devices to tissue. Other modifications and changes are readily discernible from the specification and will be apparent to those of ordinary skill.

What is claimed is:

1. An apparatus for joining at least two anatomical structures, the apparatus comprising:

a suture having a first end and a second end, the suture being constructed for passage through the at least two anatomical structures;

a needle for penetrating and passing through the at least two anatomical structures, the needle being disposed at the first end of the suture and having a sharp tip; and a holding device for holding the at least two anatomical structures together, the holding device being disposed at the second end of the suture for placement into proximity with the at least two anatomical structures, the holding device being constructed for movement from an initial configuration to a holding configuration, wherein the holding device comprises structure for contacting each of the at least two anatomical structures while simultaneously joining together the at least two anatomical structures when the holding device is in the holding configuration.

2. The apparatus of claim 1, wherein the holding device includes staple structure comprising a bendable material, movement of the holding device from the initial configuration to the holding configuration comprising bending of the staple.

3. The apparatus of claim 2, wherein the staple structure is constructed for passage into the anatomical structures, such that the staple structure substantially surrounds ends of the anatomical structures when the holding device is in the holding configuration.

4. The apparatus of claim 1, wherein the stiffness of the holding device is substantially greater than the stiffness of the suture material.

5. The apparatus of claim 1, wherein the apparatus is constructed for effecting an anastomosis of the two anatomical structures, the two anatomical structures being vascular structures.

6. The apparatus of claim 5, wherein the holding device holds the vascular structures together from inside the vascular structures.

7. The apparatus of claim 6, wherein the apparatus is constructed for effecting at least one of a side-to-side, end-to-side and end-to-end anastomosis.

8. The apparatus of claim 1, wherein the suture and holding device are constructed for ready separation from each other once the holding device is in the holding configuration.

9. The apparatus of claim 1, wherein the holding device comprises a bendable member having a cross-piece, the bendable member being bent into a crimped shape when the holding device is in the holding configuration.

10. The apparatus of claim 9, wherein the cross-piece is constructed for anchoring to at least one of the anatomical structures when the holding device is in the holding configuration.

11. The apparatus of claim 10, wherein the holding device is constructed to substantially prevent a distal portion of the holding device from tearing through the anatomical structures.

12. The apparatus of claim 1, wherein the apparatus is constructed for joining two vascular structures.

13. The apparatus of claim 1, wherein the apparatus is constructed for use in minimally invasive surgical techniques.

14. The apparatus of claim 1, wherein the suture extends parallel to the holding device at the point of attachment between the suture and the holding device.

15. The apparatus of claim 1, wherein the holding device is a surgical staple of substantially constant diameter and substantially constant cross-section along its length.

16. The apparatus of claim 1, wherein the holding device in the holding configuration is disposed both inside and outside the anatomical structures.

17. The apparatus of claim 1, wherein the suture is removable from the holding device while the holding device joins the at least two anatomical structures together.

18. A staple for effecting an anastomosis between two vascular structures in combination with a delivery system for the staple, the delivery system comprising a suture having a needle connected thereto at one end of the suture and the staple comprising two limbs, each limb defining a tip, an end of the suture opposite the one end being attached to the staple at the tip of one of the two limbs, wherein:

the needle comprises a sharp point for passage through an edge of both vascular structures and the suture is dimensioned for being pulled through the vascular structures by the needle, the vascular structures being placed in opposition to form an anastomosis;

the staple defines a hook shape for being hooked into a desired position with respect to the vascular structures such that the staple is engaged on both sides of the anastomosis;

the staple comprises a crimp opposite the tips for being crimped to form substantially a loop around the edge of the anastomosis to hold the vascular structures together; and the suture is separable from the staple once the staple is crimped, thereby separating the delivery system from the staple.

19. The combination of claim 18, wherein crimping of the staple causes the two limbs of the staple to move into proximity with each other.

20. The combination of claim 18, wherein the two limbs of the staple form a substantially acute angle before the staple is crimped.

21. The combination of claim 18, wherein the needle, suture and staple are of a substantially identical diameter.

22. The combination of claim 18, wherein the staple comprises a cross-piece constructed to lie in the plane of the anastomosis when the staple is crimped.

23. The combination of claim 18, wherein the staple is constructed for use as a pilot device to approximate the vascular structures prior to completion of the anastomosis.

24. The combination of claim 14, wherein the staple is attachable to the suture only at one point.

25. The apparatus of claim 14, wherein the two limbs of the staple are identical.

26. A method for joining at least two anatomical structures, the method comprising:

(a) penetrating the anatomical structures with a needle having a sharp tip and passing the needle through the anatomical structures;

(b) passing a suture having a first end and a second end through the anatomical structures, the needle being disposed at the first end of the suture; and (c) holding the anatomical structures together with a holding device disposed at the second end of the suture, wherein the holding step includes:

(d) placing the holding device into proximity with the anatomical structures; and (e) moving the holding device from an initial configuration to a holding configuration, movement of the holding device from the initial configuration to the holding configuration causing the anatomical structures to be joined together.

27. The method of claim 26, wherein the method includes joining the anatomical structures with at least two holding devices, the method further comprising:

(f) parachuting the sutures connected to the respective holding devices by pulling the anatomical structures apart, in order to assess proper positioning of the sutures and holding devices.

28. The method of claim 26, wherein the method includes joining the anatomical structures with at least two holding devices to approximate the structures, the method further comprising:

(f) applying biologic glue and/or laser to effect a complete anastomosis of the anatomical structures.

29. A staple for effecting an anastomosis between two vascular structures in combination with a delivery system for the staple, the delivery system comprising a suture having a needle connected thereto at one end of the suture and the staple comprising two limbs, one of the two limbs being connected to an end of the suture opposite the one end, wherein:

the needle is constructed for passage through an edge of both vascular structures and the suture is constructed for being pulled through the vascular structures by the needle, the vascular structures being placed in opposition to form an anastomosis;

the staple is constructed for being hooked into a desired position with respect to the vascular structures such that the staple is engaged on both sides of the anastomosis;

the staple is constructed for being crimped to form substantially a loop around the edge of the anastomosis to hold the vascular structures together; and the suture is constructed for separation from the staple once the staple is crimped, thereby separating the delivery system from the staple;

wherein the needle, suture and staple are of a substantially identical diameter.

* * * * *